United States Patent [19]
Haubs et al.

[11] Patent Number: 5,831,087
[45] Date of Patent: *Nov. 3, 1998

[54] MACROCYCLIC IMIDE COMPOUNDS

[75] Inventors: Michael Haubs, Bad Kreuznach, Germany; Marie Borzo, Basking Ridge, N.J.

[73] Assignee: Hoechst Celanese Corp., Somerville

[ * ] Notice: The term of this patent shall not extend beyond the expiration date of Pat. No. 5,710,241.

[21] Appl. No.: 205,056

[22] Filed: Mar. 2, 1994

[51] Int. Cl.$^6$ .................................................. C07D 487/22
[52] U.S. Cl. .......................... 540/460; 540/456; 540/465; 540/472
[58] Field of Search .................................... 540/460, 456, 540/469, 472

[56] References Cited

U.S. PATENT DOCUMENTS 5,364,614  11/1994  Platzer et al. .............................. 424/9

OTHER PUBLICATIONS

Grant & Hackh's Chemical Dictionary, 5th ed. (1987), p. 40, McGraw–Hill Book Co.
Schroff et al, Journal of the Royal Neth. Chem. Society, vol. 95, No. 4, (1976), pp. 89–93.
Kitao, Chemical Abstracts 86:44765h (1977).
Bradshaw et al, J. Heterocyclic Chem. 27, pp. 2113–2116 (1990).
Krakowiak et al, J. organic Chem. 55, pp. 3364–3368 (1990).
Greene, *Protective Groups in Organic Synthesis* (1981), pp. 232–233, 251–252.
Encyclopedia of Polymer Science and Technology, 1987 vol. 9, pp. 183–195 entitled "Macrocyclic Polymers", Rempp et al.
Moore, J. et al., "Efficient Synthesis of Nanoscale Macrocyclic Hydrocarbons", Agnew. Chem. Int. Ed. Engl. 1992, 31, No. 7, pp. 922–924 VCH (1992).
Wu, Ziyan et al., "Synthesis of Three Dimensional Nanoscaffolding", J. Am. Chem. Soc., 144 pp. 8730–8732, ACS (1992).
Bonar–Law, R.P. et al. "Morphine Recognition by a Porphyrin–Cyclocholate Modular Bowl", Chem. Comm. (1994).
Anderson, H.L. et al. Recognition of Giant Cluster Anions By A Protonated Porphyion Trimer: Detection By Fast–Atom Bondordment (FAB) Mass Spectrometry, J. Chem. Soc. Chem. Com. 1992, pp. 946–947.

*Primary Examiner*—Richard L. Raymond
*Attorney, Agent, or Firm*—Michael W. Ferrell

[57] ABSTRACT

Macrocycle compounds of precise molecular geometry are disclosed and claimed, useful for a variety of purposes including membranes, molecular recognition and any other purpose where specific molecular macrogeometry is important. Most preferably, the macrocycles are of the imide class, formed by way of reactions of diamines with α-anhydride, ω-nitro compounds, followed by cyclization with an acid chloride.

10 Claims, No Drawings

MACROCYCLIC IMIDE COMPOUNDS

CROSS REFERENCE TO RELATED APPLICATION

This application is related to a United States Patent Application being filed concurrently herewith entitled Monoanhydride Compounds, Methods of Making Same and Reaction Products Thereof, Attorney Docket No. 1490, Ser. No. 08/205,054, filed Mar. 2, 1994. The disclosure of this related application is incorporated herein by reference as if fully set forth below.

TECHNICAL FIELD

The present invention relates generally to macrocyclic compounds and in preferred modes to macrocyclic imides synthesized from reaction of α-anhydride, ω-nitro organic compounds with diamines followed by cyclization.

BACKGROUND

Macrocyclic compounds have long been of interest due to their unique characteristics as opposed to linear polymers of like molecular weights. The lack of end groups influences melt viscosity and thermo-mechanical behavior in the bulk. Because of low hydrodynamic volume and high segment densities, macrocyclic polymers tend to exhibit low limiting viscosity numbers as well as low frictional coefficients.

Moreover, macrocyclic compounds have been recognized as having particular utility by virtue of their well-defined microstructure, especially in the area of recognition and selective complexation See Moore, J. et al. "Efficient Synthesis of Nanoscale Macrocyclic Hydrocarbons", Angew. Chem. Int. Ed. Engl., VCH (1992), pp. 922–924; Moore, J. et al. "Synthesis of Three Dimensional Nanoscaffolding", J. Am. Chem. Soc., 114, pp. 8730–8732, ACS (1992); Bonar-Law, R. P. et al., "Morphine Recognition by a Porphyrin-Cyclocholate Molecular Bowl", Chem. Comm. (1993 pp. 456–458); and Anderson, H. L. et al. "Recognition of Grant Cluster Anions by a protonated Porphyrin Trimer: Detection by Fast Atom Bombardment (FAB) Mass Spectrometry", Chem Comm. (1992).

Such materials indeed have untapped potential in a plethora of applications such as membranes for gas separation, ultrafiltration, chiral separation or any other application where precise molecular geometry is important.

The present invention provides a method to make macrocycles with precise molecular geometry as well as such compounds.

Precursor compounds, such as alkylated aromatic amines and nitro compounds useful in connection with the present invention are well known in the art. For instance, the literature describes the alkylation of such compounds as follows:

N,N-Bis(4-nitrophenyl)-alkylamines. In a typical instance, N,N-Bis(4-nitrophenyl)-amine (20 g), n-octyl iodide (19 g), potassium hydroxide (5·1 g), water (5.2 ml) and acetone (200 ml) were heated to reflux for 2 h and then poured into water (800 ml). The precipitated solid was washed with 50 percent aqueous ethanol (50 ml) and then with ether (50 ml). Recrystallization from ethanol afforded yellow leaflets. Kloetzel, M. et al. Potential Chemotherapeutic Compounds-III-Derivatives of 2-aminodiphenyl and N,N,-Bis(4-aminophenyl)-alkylamines. Journal of Medicinal and Pharmaceutical Chemistry Vol. 1 No. 3 (1959), p. 206.

SUMMARY OF INVENTION

There is provided in accordance with the present invention a method of synthesizing a sequenced macrocycle compound including preparing a compound of the formula:

where X is a nitro substituent or a protected amino substituent, Y is a substituent capable of reacting with an amine selected from the group consisting of acid anhydrides, acid chlorides, acid imidazolides, sulfonyl chlorides, isocyanates and carboxylic acids, and R is a substituted or unsubstituted aromatic nucleus with a molecular weight of at least about 150; reacting said compound with a diamine to form a first reaction product wherein the X functionalities of said compound are unreacted; converting the X functionalities of said first reaction product to amino groups to form a second reaction product; and cyclizing said second reaction product to form the macrocycle.

In particularly preferred methods the macrocycles are prepared by ring closing reactions of oligomer diamines with acid dichlorides. The oligomer diamines are synthesized starting from a diamine as well as an anhydride and growing the molecule. To this end, there was reacted a diamine with an α-nitro, ω-anhydride building block. After condensation imidization the terminal nitro groups were reduced to give the trimer diamine. This process was then repeated to give the pentamer diamine.

In the following description this synthesis is described using N,N-Bis(4-aminophenyl)dodecylamine as the diamine and a suitable anhydride building block.

Particular compounds of the present invention are likewise disclosed and claimed in the material following.

BRIEF DESCRIPTION OF DRAWINGS

The invention is described hereafter in connection with drawings in which:

FIG. 1 is a diagram illustrative of the chemical structure of the macrocycle compounds of the present invention synthesized in accordance with Example 7; and FIG. 2 is a diagram illustrating the chemical structure of the macrocycle compound synthesized in accordance with Example 8.

DETAILED DESCRIPTION

The invention is described in detail below with reference to numerous examples which are provided for purposes of illustration only. The invention relates generally to macrocycle compounds as one of skill in the art will readily appreciate. The inventive compounds are generally synthesized by preparing a compound of the formula:

where X is a nitro substituent or a protected amino substituent, Y is a substituent capable of reacting with an amine selected from the group consisting of acid anhydrides, acid chlorides, acid imidazolides, sulfonyl chlorides, isocyanates and carboxylic acids, and R is a substituted or unsubstituted aromatic nucleus with a molecular weight of at least about 150; reacting the compound with a diamine to form a first reaction product wherein the X functionalities of said compound are unreacted; converting the X functionalities of the first reaction product to amino groups to form a second reaction product; and cyclizing the second reaction product to form the macrocycle. A protected amine can be formed by reaction of an amine with τ-butylchloroformate or τ-butylazidoformate to form the τ-butyloxycarbonyl derivative or by reaction with sulfonyl chloride, benzylchloride, or acetylchloride which forms the acetamide.

Most preferably Y is a carboxylic acid anhydride.

The step of cyclizing the second reaction product may include reacting the second reaction product with a compound selected from the group consisting of tetraacid anhydrides and diacid chlorides. R is most preferably an alkyl substituted aromatic nucleus.

A sequenced macrocycle pentamer compound in accordance with the invention may be made by preparing a first compound of the formula

where X is a nitro or a protected amino substitutent, Y is a substituent capable of reacting with an amine selected from the group consisting of acid anhydrides, acid chlorides, imidazolides, sulfonyl chlorides, isocyanates and carboxylic acids and R is an organic radical; reacting two equivalents of the first compound with a first diamine to form a first trimer, wherein the X functionalities of said compound are unreacted; converting the X functionalities of the first trimer to amino groups to form a second diamine trimer; reacting the second diamine trimer with two equivalents of a second compound of the formula

to form a pentamer, wherein X and Y are defined as above and wherein the X functionalities are unreacted; converting the X functionalities of the pentamer to amino groups to form a pentamer diamine; and cyclizing said pentamer diamine.

Preferably, the first compound referred to immediately above includes the structural unit:

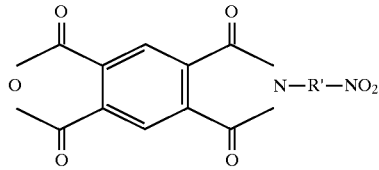

wherein R' is an organic radical.

This may include the structural unit:

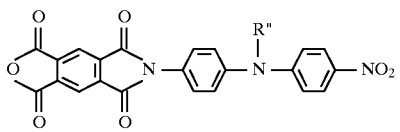

wherein R" is a $C_1$–$C_{18}$ alkyl chain.

In another aspect of the present invention there is provided oligomeric compound of the formula:

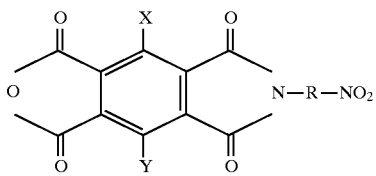

wherein R is an organic radical having a molecular weight of from about 50 to about 1000 and X and Y are independently hydrogen, a halogen, an organic radical, or a sulfur containing radical.

The oligomeric compound may have an R substituent with a molecular weight of from about 100 to about 300 and may include the residue of a compound of the formula:

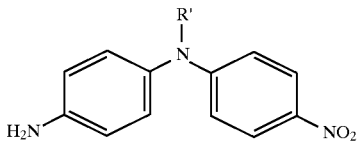

wherein R' is a $C_1$–$C_{18}$ alkyl group.

The imide macrocycles of the present invention include the substructural unit:

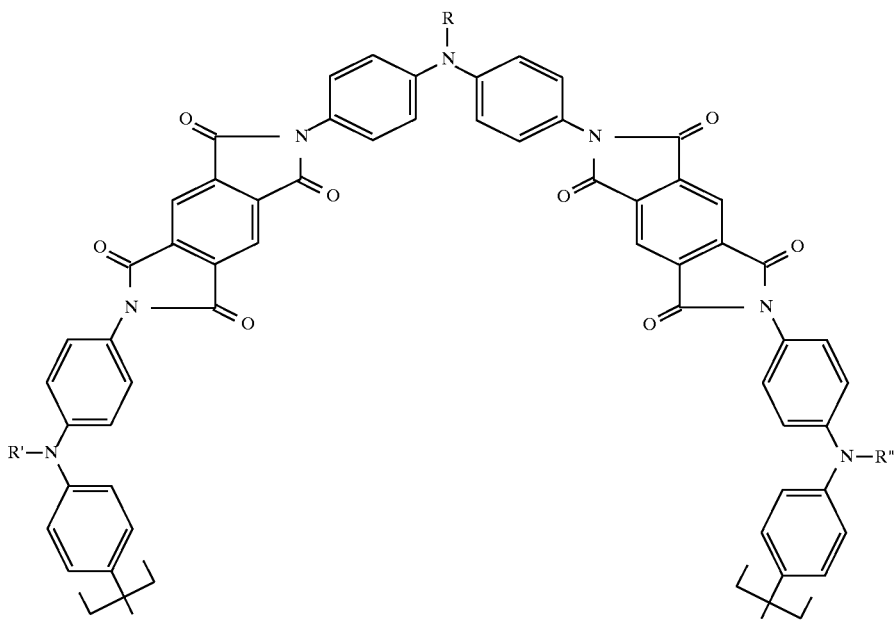

where R,R' and R" are the same or different and are $C_1$–$C_{18}$ alkyl groups and may include the residue of at least two additional α-nitro, ω-anhydride compounds. Compounds of the present invention may of course be formed into a film or other shaped article as desired.

The macrocycles are most preferably prepared by ring closing reactions of oligomer diamines with acid dichlorides.

The oligomer diamines are synthesized starting from a diamine and nitro anhydrides and growing the molecule from both ends. To that end, the diamine is reacted with an α-nitro ω-anhydride building block. After condensation imidization the terminal nitro groups are reduced to give the trimer diamine. This process was then repeated to give the pentamer diamine.

In the following the macrocycle synthesis is described using N,N-Bis(4-aminophenyl)dodecylamine as the diamine and the following compound as the α-nitro ω-anhydride building block:

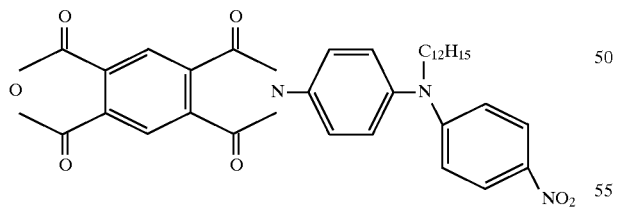

The above compound will be referred to in the following as NABB.

EXAMPLE 1

Preparation of the α-Nitro-ω-Anhydride Building Block (NABB)

Reaction of Pyromellitic Monoanhydride (PMMA) with N,N-(4-amino,4'-nitrodiphenyl)dodecylamine (ANDA)

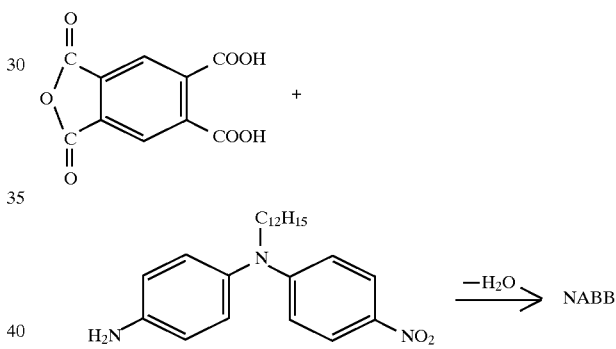

N,N-(4-amino,4'-nitrodiphenyl)dodecylamine (ANDA) was prepared by alkylating the appropriate diphenyl amine following literature procedures (M. C. Kloetzel et al. J. Med. Pharm. Chem. 1, 197–211 (1959).

Pyromellitic monoanhydride was prepared as follows:

26 g (0.12 mol) of PMDA are dissolved in 200 ml of a 1:1 mixture of 1-Methyl-2-pyrrolidinone (NMP) and N,N-Dimethylacetamide (DMAc) at 25° C. with stirring. To the clear solution is added 2.80 g (0.16 mol) of water in 40 ml of NMP. The temperature of the reaction mixture is kept at 25° C. for 15 minutes (cooling). The temperature is then lowered by 5° C. every 15 minutes. After 1 hour (T=5° C.) the flask is put into an ice bath and kept at –10° C. for 4 hours.

38 g (0.096 mol) of ANDA are added in portions with stirring to the cold mixture. 5 minutes after the solid is completely dissolved, 18 g (0.19 mol) of 3-picoline and 35 g (0.34 mol) of acetic anhydride are added. The solution is allowed to stand overnight at room temperature. The clear yellow solution is then poured in a fine stream into a well stirred mixture of 700 ml of water, 700 g of ice and 25 ml of conc. HCl.

After 2 mintues, the precipitate is extracted with 700 ml of methylene chloride. The organic layer is separated and washed with 300 ml of water and 100 g of ice. To the dried ($Na_2SO_4$) organic phase 10 g of acetic anhydride and 3 g of 3-picoline are added. About half the solvent is removed using a rotary evaporator. The solution is cooled in a dry ice acetone bath until crystals begin to separate. It is then allowed to stand overnight at −15° C. and filtered while cold. The crystals are washed with 50 ml of cold toluene and dried in a vacuum oven at 35° C. with nitrogen bleed. The yield is 43 g.

The structure of this compound was confirmed by 1H-NMR in $CD_2Cl_2$ it showed a singlet at 8.56 ppm, and four doublets at 8.05 ppm, 7.58 ppm, 7.42 ppm and 6.78 ppm, respectively. The alkyl chain gave a triplet at 3.81 ppm for the N—$CH_2$— protons, a multiplet at 1.74 ppm for the next —$CH_2$—, a multiplet at 1.27 ppm for the bulk of the alkyl chain and a triplet of 0.88 ppm for the terminal —$CH_3$ group. The intensities of all the peaks were consistent with the proposed structure.

EXAMPLE 2

Preparation of the Dinitro-Trimer

N,N-Bis(4-aminophenyl)dodecylamine (DADPA) was prepared following literature procedures (Kloetzel et al.).

A solution of 18 g (49 mmol) of DADPA in 80 ml of dry DMAc is added to a solution of 61.4 g (0.10 mol) of NABB of Example 1 in 310 ml of dry DMAc. The solution is stirred for 10 minutes and then 12.5 g (0.12 mol) of acetic anhydride and 25 g (0.27 mol) of 3-picoline are added. The red solution is allowed to stand overnight. Then 30 g of conc. HCl and 30 g of ethanol are added.

After stirring the solution for 20 minutes, 400 ml of ethanol are added with stirring. The precipitated product is filtered, washed with ethanol until the filtrate is clear and redissolved in 400 ml of $CH_2Cl_2$. To the clear deep yellow solution ethanol is added until a precipitate begins to appear (about 200 ml). The mixture is then cooled to 0° C. with stirring to yield a bright yellow precipitate. After storing the mixture at −15° C. for 2 hours it is filtered and washed with $CH_2Cl_2$: ethanol (1:1). The product is dried at 50° C. in a nitrogen stream. The yield is 61.5 g (82%).

TLC of the product in $CHCl_3$ (containing 1% ethanol) reveals a single spot. The 1H-NMR in $CD_2Cl_2$ shows a singlet at 8.46 ppm for the PMDA-protons, six doublets for the aromatic protons at 8.06 ppm, 7.60 ppm, 7.42 ppm, 7.40 ppm, 7.23 ppm and 6.68 ppm, respectively. The alkyl chains give a triplet at 3.82 ppm, two multiplets at 1.76 ppm and 1.28 ppm, and a triplet at 0.88 ppm. The intensities are consistent with the proposed structure.

EXAMPLE 3

Preparation of the Diamino-Trimer 17 g of glacial acetic acid are added to the clear yellow solution of 25 g dinitro-halfring (Example 2 material) in 250 ml of $CH_2Cl_2$ with stirring.

After adding 7 g of catalyst (5% Pd on activated carbon) the mixture is hydrogenated for 2.5 hours at a hydrogen pressure of 80 psi. (Hydrogen uptake levels fall off at the calculated value after about 90 minutes.) The slightly warm solution is then filtered to remove the catalyst (it can be reused) and the filtrate is concentrated to about 150 ml using a rotary evaporator. 150 ml of ethanol are added to the red-brown solution with stirring. On cooling to 5° C. a slightly brownish solid precipitates. It is filtered, washed with ethanol and dried at 45° C. in a nitrogen stream overnight. The yield is 23 g (96%). The solid compound is stable at room temperature in air; it decomposes however at temperatures over 100° C.

The TLC of the compound in $CHCl_3$ (1% ethanol) on silica gel shows a single peak. It is red-brown initially but turns dark with time. The structure of the compound is confirmed by 1H-NMR.

EXAMPLE 4

Synthesis of the Dinitro Pentamer

This reaction is essentially the same as described in Example 2. A solution of 33.9 g (23 mmol) of the diamino-trimer of Example 3 in 300 ml of DMAc are added to a solution of 28 g (47 mmol) NABB in 280 ml of DMAc with stirring. After 10 minutes, 6 g (59 mmol) of acetic anhydride and 12 g (0.13 mol) of 3-picoline are added and the solution is allowed to stand overnight.

Then 10 g of ethanol are added followed by 200 ml of DMAc 30 minutes later. To this clear deep yellow solution 600 ml of acetone are slowly added to precipitate the dinitro pentamer. It is filtered, washed with acetone and dried at 50° C. The structure is confirmed by 1H-NMR.

EXAMPLE 5

Synthesis of the Diamino Pentamer

This reaction is similar to Example 3. 8.1 g of the dinitro pentamer of Example 4 are dissolved in 250 ml of $CH_2Cl_2$ and then 30 g of acetic acid are added. 5 g of the triethylamine are added in small portions with cooling. Finally, 10 g of catalyst (5% Pd on activated carbon) are added and the mixture is hydrogenated at 80 psi for 3 hours. The catalyst is removed by filtration and the filtrate concentrated to about 200 ml. Then 150 ml of ethanol are added and the mixture is cooled to 5° C. upon which a precipitate separates. It is filtered, washed with ethanol and dried at 35° C. The yield is 7 g.

The structure is confirmed by 1H-NMR.

EXAMPLE 6

Synthesis of Macrocycle 1

A solution of 1.2 g (0.47 mmol) of the diamino pentamer of Example 5 in 45 ml of NMP and a solution of 95 mg (0.47) of terephthaloyl chloride in 22.5 ml of $CH_2Cl_2$ are added with stirring to 45 ml of DMAc at rates of 2 $\mu$l/sec and 1 $\mu$l/sec, respectively. After about 10 minutes a crystalline precipitate begins to separate. After the addition is complete the crystalline precipitate is filtered and washed with DMAc and dried at 80° C. in a vacuum oven with nitrogen bleed. The yield is 1 g. The compound is purified by recrystallization from DMAc.

The structure is confirmed by 1H-NMR.

EXAMPLE 7

Synthesis of Macrocycle 2

The procedure of Example 6 is repeated except that 163 mg of 2,5-Bis(ethoxycarbonyl)terephthaloyl chloride are used instead of 95 mg of terephthaloyl chloride. The yield is 1 g. (2,5-Bis(ethoxycarbonyl)terephthaloyl chloride was prepared according to literature procedures: H. W. Schmidt et al. Macromolecules, Vol. 25, 6789 (1992).

The compound gave consistent 1H-NMR and 13C-NMR spectra. The structure is illustrated in FIG. 1.

EXAMPLE 8

Synthesis of Macrocycle 3

The procedure of Example 6 is repeated. However 1 g of the diamino trimer and 237 mg of 2,5-Bis(carbonylethoxy) terephthaloyl chloride are used. The crystalline precipitate consists of a mixture which could be separated by recrystallization or preparative GPC. The main product is the six membered ring shown in FIG. 2.

What is claimed:

1. A method of preparing a macrocyclic compound comprising the steps of:

(a) preparing an aromatic tetracarboxylic monoanhydride-diacid compound, said tetracarboxylic monoanhydride-diacid compound being characterized in that it is provided with a single cyclic dicarboxylic acid anhydride moiety and additionally is provided with two carboxylic acid moieties capable of forming a cyclic dicarboxylic acid anhydride moiety;

(b) reacting the aromatic tetracarboxylic monoanhydride-diacid compound with a suitable amine, wherein said suitable amine includes a reactive amine moiety and a moiety selected from the group consisting of nitro substituents and protected amino substituents, and wherein further said suitable amine reacts selectively with the cyclic dicarboxylic acid anhydride moiety of said aromatic tetracarboxylic monoanhydride diacid compound to form a tetracarboxylic amide-acid-diacid intermediate;

(c) dehydrating said tetracarboxylic amide-acid-diacid intermediate to form a corresponding imide-anhydride intermediate wherein said imide-anhydride intermediate includes said nitro substituent or said protected amino substituent and a single cyclic dicarboxylic acid anhydride moiety;

(d) reacting the imide-anhydride intermediate of step (c) with one half an equivalent of diamine to form a first trimer intermediate wherein said diamine selectively reacts with the cyclic dicarboxylic acid anhydride moiety of said imide-anhydride moiety, and wherein said first trimer intermediate includes two substituents selected from the group consisting of nitro substituents and protected amine substituents;

(e) converting the substituents selected from the group consisting of nitro substituents and protected amine substituents of said first trimer intermediate to amine functionalities whereby a second trimer intermediate is formed; and (f) cyclizing said second trimer intermediate to form the macrocycle.

2. The method according to claim 1, wherein said protected amino substituent of step (c) is a t-butyloxy carbonyl derivative.

3. The method according to claim 1, wherein said protected amino substituent of step (c) is an acetamide.

4. The method according to claim 1, wherein said step of cyclizing said second trimer includes reacting said second trimer with a compound selected from the group consisting of tetracarboxylic acid anhydrides and diacid chlorides.

5. A method of preparing a macrocyclic compound comprising the steps of:

(a) preparing an aromatic tetracarboxylic monoanhydride-diacid compound, said tetracarboxylic monoanhydride-diacid compound being characterized in that it is provided with a single cyclic dicarboxylic acid anhydride moiety and additionally is provided with two carboxylic acid moieties capable of forming a cyclic dicarboxylic acid anhydride moiety;

(b) reacting the aromatic tetracarboxylic monoanhydride-diacid compound with a suitable amine, wherein said suitable amine includes a reactive amine moiety and a moiety selected from the group consisting of nitro substituents and protected amino substituents, and wherein further said suitable amine reacts selectively with the cyclic dicarboxylic acid anhydride moiety of said aromatic tetracarboxylic monoanhydride diacid compound to form a tetracarboxylic amide-acid-diacid intermediate;

(c) dehydrating said tetracarboxylic amide-acid-diacid intermediate to form a corresponding imide-anhydride intermediate wherein said imide-anhydride intermediate includes said nitro substituent or said protected amino substituent and a single cyclic dicarboxylic acid anhydride moiety;

(d) reacting the imide-anhydride intermediate of step (c) with one half an equivalent of diamine to form a first trimer intermediate wherein said diamine selectively reacts with the cyclic dicarboxylic acid anhydride moiety of said imide-anhydride moiety, and wherein said first trimer intermediate includes two substituents selected from the group consisting of nitro substituents and protected amine substituents;

(e) converting the substituents selected from the group consisting of nitro substituents and protected amine substituents of said first trimer intermediate to amine functionalities whereby a second trimer intermediate is formed; and (f) reacting said second trimer intermediate with an imide-anhydride intermediate formed by following the procedure of steps (a) through (c) above to form a first pentamer intermediate;

(g) converting the substituents selected from the group consisting of nitro substituents and protected amine substituents of said first pentamer intermediate to amine functionalities whereby a second pentamer intermediate is formed; and (h) cyclizing said second pentamer intermediate.

6. The method according to claim 5, wherein said step of cyclizing said second pentamer intermediate comprises reacting said second pentamer intermediate with a diacid chloride.

7. The method according to claim 5, wherein said imide-anhydride intermediate has the structure formula:

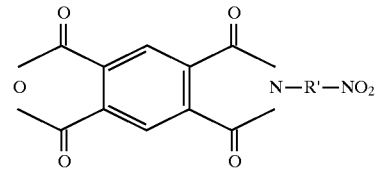

wherein R' is an organic radical.

8. The method according to claim 7, wherein said imide-anhydride intermediate has the structural formula

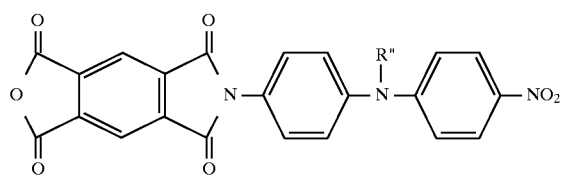
wherein R" is a $C_1$–$C_{18}$ alkyl chain.
9. The method according to claim 5, wherein said protected amino substituent of step (c) is a t-butyloxy carbonyl derivative of an amino group.
10. The method according to claim 5, wherein said protected amino substituent of step (c) is an acetamide.
* * * * *